United States Patent
Miller

(10) Patent No.: US 7,766,235 B2
(45) Date of Patent: Aug. 3, 2010

(54) COMBINED RADIO FREQUENCY IDENTIFICATION AND OPTICAL IMAGING MODULE

(75) Inventor: David Paul Miller, Brewerton, NY (US)

(73) Assignee: Jadak Technologies, Inc., Liverpool, NY (US)

( * ) Notice: Subject to any disclaimer, the term of this patent is extended or adjusted under 35 U.S.C. 154(b) by 215 days.

(21) Appl. No.: 11/308,170

(22) Filed: Mar. 9, 2006

(65) Prior Publication Data

US 2007/0210158 A1    Sep. 13, 2007

(51) Int. Cl.
G06K 7/06 (2006.01)
G06K 7/04 (2006.01)

(52) U.S. Cl. .................... 235/440; 235/445

(58) Field of Classification Search ............... 235/440, 235/445
See application file for complete search history.

(56) References Cited

U.S. PATENT DOCUMENTS

| | | | |
|---|---|---|---|
| 6,127,928 A * | 10/2000 | Issacman et al. ......... 340/572.1 |
| 6,501,382 B1 | 12/2002 | Rehufus et al. |
| 2002/0063622 A1 * | 5/2002 | Armstrong et al. ....... 340/10.31 |
| 2003/0095525 A1 | 5/2003 | Lavin et al. |
| 2003/0132298 A1 | 7/2003 | Swartz et al. |
| 2004/0118920 A1 | 6/2004 | He et al. |
| 2004/0177032 A1 | 9/2004 | Bradley et al. |
| 2005/0120260 A1 * | 6/2005 | Suzuki et al. ................. 714/5 |
| 2005/0144044 A1 | 6/2005 | Godschall et al. |
| 2005/0150959 A1 | 7/2005 | Izzo et al. |
| 2005/0156040 A1 | 7/2005 | Young et al. |
| 2005/0184160 A1 | 8/2005 | Steinmetz et al. |
| 2005/0203941 A1 | 9/2005 | Polarine et al. |
| 2005/0282603 A1 | 12/2005 | Parrott et al. |
| 2006/0023930 A1 | 2/2006 | Patel et al. |
| 2006/0109119 A1 * | 5/2006 | Burr et al. ................ 340/572.1 |
| 2006/0113374 A1 * | 6/2006 | Taylor et al. ................. 235/376 |
| 2008/0180215 A1 * | 7/2008 | Mott .......................... 340/10.1 |
| 2009/0266898 A1 * | 10/2009 | Miller et al. ............ 235/472.01 |
| 2009/0289116 A1 * | 11/2009 | Copeland et al. ............. 235/440 |

FOREIGN PATENT DOCUMENTS

WO    WO2004059563    6/2004

* cited by examiner

*Primary Examiner*—Thien M Le
(74) *Attorney, Agent, or Firm*—David L. Nocilly; George R. McGuire; Bond Schoeneck & King, PLLC

(57) ABSTRACT

An optical imager, a RFID reader, and a single host interface combined into a single module for use as a stand alone device or OEM product. The module includes a system microcontroller that interconnects an optical image microcontroller and a RFID microcontroller through the single interface to a host device, such as a computer. The system microprocessor is configurable via the host interface to selectively provide RFID reading, optical imaging, or a variety of combinations of both techniques. The module is programmable to allow the host computer trigger the RFID reader and optical imager. In addition, the system microcontroller is programmable via the host computer to provide image analysis, such as shape determination or recognition, prior to relaying data to the host computer through the single interface.

19 Claims, 4 Drawing Sheets

COMBINED RADIO FREQUENCY IDENTIFICATION AND OPTICAL IMAGING MODULE

FIELD OF INVENTION

The present invention relates to data collection systems and, more specifically, to a system and method for combining radiofrequency identification and optical imaging into a host controllable module.

DESCRIPTION OF PRIOR ART

Barcodes are essentially graphic representation of data (alpha, numeric, or both) that is machine-readable. Barcodes encode numbers and letters into different types of symbologies, such as linear codes, two-dimensional codes, and composite codes (a combination of linear and two-dimensional codes). In more recent applications, referred to as digital or optical image capture, an optical device snaps a digital picture of the barcode and software in the imager orients the picture and decodes the barcode(s) contained in the picture.

Radiofrequency identification (RFID) is a wireless communication technology that utilizes radiowaves for automatic identification and data capture of information for the purpose of identifying and tracking objects, people, or even animals. Signals in the radio frequency (RF) range of the electromagnetic spectrum are used to communicate data between a two transceiver devices. An RFID system typically consists of the three main components: a tag, a reader, and the software/firmware for controlling the system. Tags are placed on objects or people and directly or indirectly contain information about the object or person. The reader uses RF energy to interrogate the tag and read the information it contains, or even write data to the tag.

Technologies such as barcode imaging and RFID can play an important role in various fields by automating processes and improving safety and security. For example, the ability to more accurately track objects and instantly provide data about the object is becoming a particularly important tool in the medical field, where automated systems can help improve safety procedures and limit human errors. In one such system, medical samples and prescription medication may often be provided with a barcode to assist with tracking the formulation and delivery of the medication or samples, and proper identification of the patient to whom the medication or samples belong. RFID technology may be used for tracking medical devices to ensure that the right device is available to the correct patient at the correct time, servicing and administering drugs, or to track the location of high-risk devices like implants that may relocate within a patient.

Conventional systems for utilizing barcodes and RFID are often rudimentary, particularly in the medical field. For example, some system use an array of photo sensors to detect the presence of medical devices. However, the information recognized by these systems is simply the presence of absence of the device or predetermined indicia. As a result, there is no true image data, the systems lack the ability to process images, and the methods used to communicate the results to the host system are rather limited. In addition, it is often not practical or easy to place indicia on devices that, for example, must withstand the temperatures and process of sterilization. Moreover, the process or expense necessary of accurately place indicia or RFID tags on legacy medical devices may outweigh the feasible of using more advanced systems.

Bar code identification systems and RFID systems generally require middleware applications that provide an interface between the readers and the host device or computer. The middleware filters and structures the data read from the tags and integrates it into the host application, which stores the information from the tag or dictates the action to be taken with the information. Middleware and host data management software applications are usually provided by an RFID vendor or by third party applications developers. These systems are not, however, capable of combining the advantages of machine vision and RFID into a modular package that may be easily integrated into existing medical devices or adapted for use in new systems and easily controlled by the user. Instead, they require the integration of multiple systems and the use of sophisticated processing software to accomplish any functions beyond rudimentary barcode identification and RFID interrogation.

SUMMARY OF THE INVENTION

It is a principal object and advantage of the present invention to provide a modular and scalable system that combines RFID and optical imaging capabilities.

It is an additional object and advantage of the present invention to provide a modular and scalable system that combines RFID and optical imaging capabilities that is controllable via a host computer.

It is a further object and advantage of the present invention to provide a modular and scalable system that combines RFID and optical imaging capabilities that is field programmable.

It is another object and advantage of the present invention to provide a field programmable module capable of custom image processing.

Other objects and advantages of the present invention will in part be obvious, and in part appear hereinafter.

In accordance with the foregoing objects and advantages, the present invention comprises a modular and scalable system for integrating two or more subsystems into a host controlled device. More particularly, the present invention is capable of integrating an optical imager and a RFID reader with a single host interface. The invention includes a system microcontroller that interconnects an optical image capture subsystem and a RFID subsystem through a single interface to a host computer. The system microprocessor is configurable via the host interface to selectively provide RFID reading or writing, optical imaging, barcode reading, or a variety of combinations of both techniques. The module is programmed to allow the host computer to trigger the RFID reader and optical imager. In addition, the system microcontroller is programmable via the host computer to provide image analysis, such as shape determination or recognition, prior to relaying data to the host computer through the single interface. Further, the implementation of each of the interfaces to imager, host computer, and RFID functions can be configured to be physically and electrically identical. This variations in the functionality delivered by the module while maintaining a single connection to the host compture. The present invention may be easily retrofit into a pre-existing system and programmed to perform a variety RFID and optical imaging tasks previously unavailable to the system, or easily integrated into a new system without the need for additional hardware and software for performing image and interrogation data processing.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
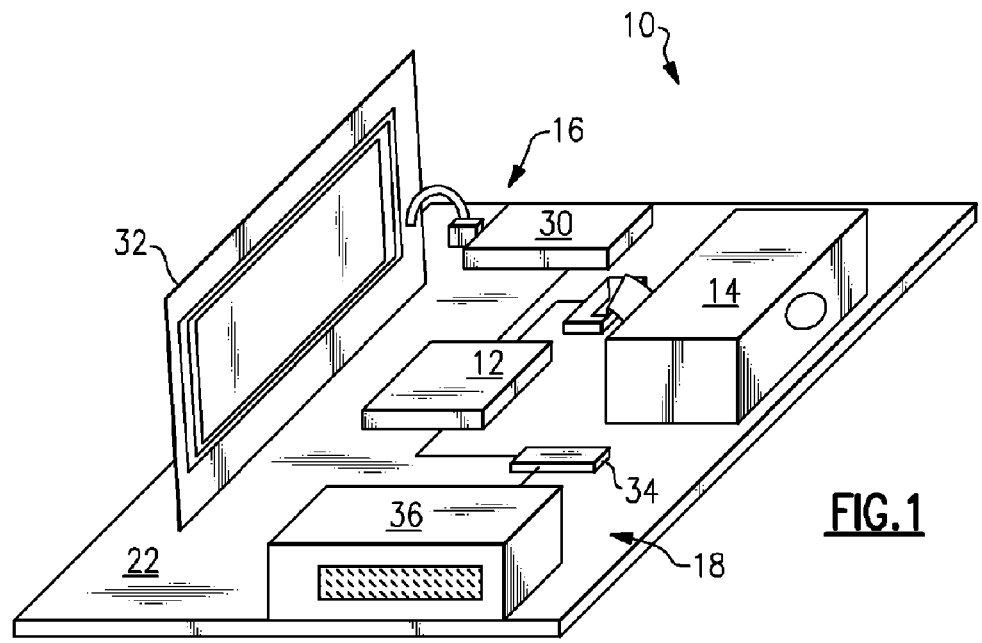
FIG. 1 is a perspective view of a combined RFID and optical imager according to the present invention.

Referring now to the drawings, wherein like numerals refer to like parts throughout, there is seen in FIG. 1 a combined RFID and optical image module 10 according to the present invention. Module 10 generally comprises a microcontroller 12 that interconnects a first submodule, such as an optical imager 14, and a second submodule, such as a RFID unit 16, to a single host interface 18. Alternatively, module 10 is capable of interconnecting any variety of data capturing devices as submodules and providing host controllability, including optical imagers, RFID transceivers, lasers, scales, thermometers or temperature probes, etc., in any variety of combinations. Module 10 may be arranged on a single printed circuit board 22 and encased as a single unit or housing. Integration of imager 14 and RFID unit 16 through interface 18 allows for combining control of operation of both submodules, such as RFID reading and barcode, through module 10, as will be explained in detail hereinafter.

Figure 2:
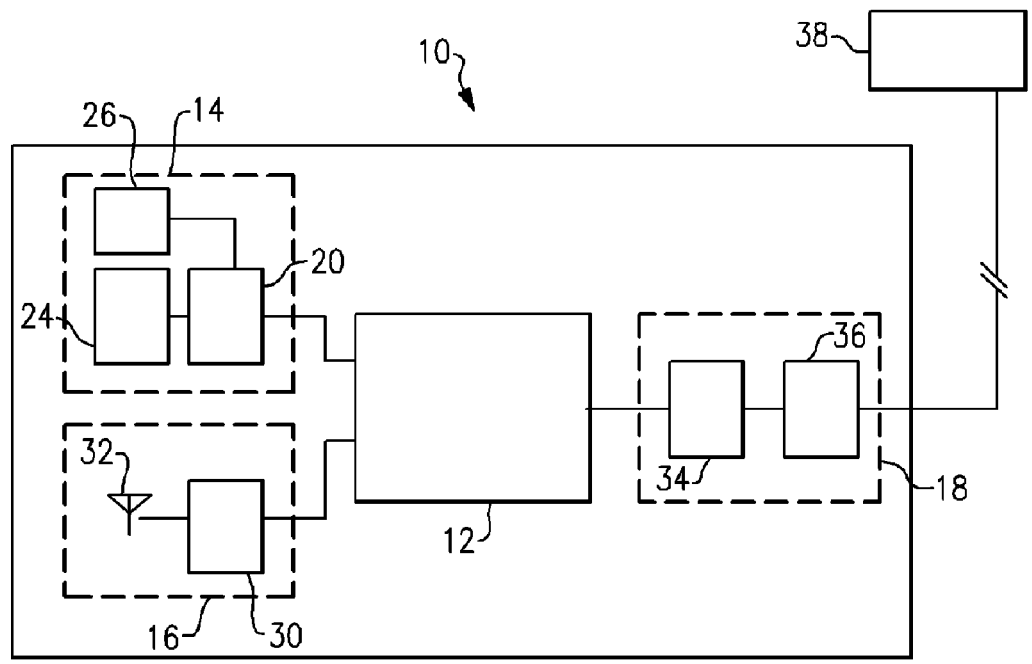
FIG. 2 is a schematic of a combined RFID and optical imager according to the present invention.

Referring to FIG. 2, a first submodule of module 10 is illustrated as an optical imager 14 comprising an image engine 20 having image processing circuitry interconnected to microcontroller 12 for omni-directional optical scanning. Image engine 20 controls an image sensor 24, such as a complementary metal oxide semiconductor (CMOS) image sensor, and is capable of capturing two-dimensional images of 1D linear barcodes, 2D stacked/matrix barcodes, standard optical character recognition (OCR) fonts, Reduced Space Symbology (RSS) barcodes, and postal barcodes, as well as providing image captured images for use in a wide range of applications, such as image and shape recognition, signature capture, image capture, and non-standard optical character recognition. Imager 14 may further include an integrated illumination source 26 connected to engine 20, such as one or more light emitting diodes (LEDs) of various wavelengths, to enhance illumination, operation, and image capture. For example, module 10 may include red LEDs for general illumination and green LEDs for targeting. Imager 14 may comprise, but is not limited to, an IT4X10/80 SR/SF or IT5X10/80 series imager available from Hand Held Products, Inc. of Skaneateles Falls, N.Y. that is capable of scanning and decoding most standard barcodes including linear, stacked linear, matrix, OCR, and postal codes. Specifically, the IT5X10/80 series imager is a CMOS-based decoded output engines that can read 2D codes, and has image capture capabilities sufficient for use with module 10.

Imager 14 obtains an optical image of the field of view and, using preprogrammed algorithms in image engine 20, deciphers the context of the image to determine the presence of any decodable barcodes, linear codes, matrix codes, and the like. Image engine 20 may be programmed to perform other image processing algorithms on the image captured by imager 14, such as shape recognition, match filtering, statistical analysis (e.g., threshold detection), and other high-level processing techniques. Alternatively, a captured image may be processed by microprocessor 12, albeit with a decreased level of performance due to the additional communication time needed to transfer images from image engine 20 to microprocessor 12.

Second submodule of module 10 may comprise an RFID unit 16 including a RFID transceiver 30 and associated RFID antenna 32 supporting standard RFID protocols, such as the TI Tag-it transponder protocol or ISO 15693. For these protocols, transceiver 30 operates at 13.56 MHz, and may comprise a S6700 Multi-Protocol Transceiver IC available from Texas Instruments of Dallas, Tex. Depending on the application, other frequency transceivers may be more appropriate based on target range, power availability, cost, etc. RFID unit 16 may further include a speaker or LED (not shown) for audibly indicating a successful interrogation of a RFID tag.

Antenna 32 is preferably a loop antenna of various sizes and turns implemented on a printed circuit board and connected to module 10, or a wire loop installed antenna installed directly onto module 10. Antenna 32 may be positioned remotely, thereby reducing the footprint of module 10 using an external connector, such as a MMCX coaxial connector. RFID transceiver 30 may be programmed to interrogate passive or active tags, process signals received from such tags (e.g., analog to digital conversion), and provide the information from the tags to microcontroller 12 for further processing or transmittal to a host computer via interface 18.

Host interface 18 comprises a host transceiver 34 and a host connector 36 for interconnection to a host device 38. Interface 18 may comprise a conventional RS232 transceiver and associated 12 pin RJ style jack. For example, an ADM202EARN available from Analog Devices, Inc. of Norwood, Mass. is a suitable RS-232/V.28 interface device having compliant levels of electromagnetic emissions and immunity. Alternatively, interface 18 may comprise other conventional buses, such as USB, IEEE 1394, I2C, SPI, or PCMCIA, or other connector styles, such as an FFC style to an embedded host or another module 10. Interface 18 may also comprise a wireless transceiver in lieu of connector 36 for wireless communication to a host computer. A Stewart Connector Systems Inc. SS-641010S-A-NF may serve as connector 36 for mating with a Stewart Connector 937-SP-361010-031 matching connector of a host device. Host interface 18 may also comprise a Molex MX52588 connector. Regardless of the type of connector 36 used, host transceiver 34 is programmed with the applicable protocols for interfacing with a host computer, such as USB, Bluetooth(r), and IrDA protocols. Transceiver 34 may also be programmed to support both non-inverted signal sense and inverted signal sense.

Microcontroller 12 comprises a conventional programmable microprocessor having on-chip peripherals, such as central processing unit, Flash EEPROM, RAM, asynchronous serial communications interface modules, serial peripheral interfaces, Inter-IC Buses, timer modules, pulse modulators with fault protection modules, pulse width modulators, analog-to-digital converters, and digital-to-analog converters. Additionally, the inclusion of a PLL circuit allows power consumption and performance to be adjusted to suit operational requirements. In addition to the I/O ports dedicated I/O port bits may be provided. Microcontroller 12 may further include an on-chip bandgap based voltage regulator that generates an internal digital supply voltage from an external supply range. Microcontroller 12 preferably comprises a Motorola MC9S12E128.

The functional integration of imager 14 and RFID unit 16 to interface 18 is accomplished by microcontroller 12, which receives and interprets host commands, and then executes the appropriate functions by driving imager 14 and/or RFID unit 16 accordingly. For example, the operation of imager 14 and RFID unit 16 may be triggered by serial commands sent to module 10 from a host device 38, or by a hardware button communicating directly with connector 36 or through host device 38. Microcontroller 12 may further be programmed to execute the functions otherwise performed by one or more of image engine 20, RFID transceiver 30, and host transceiver 34, thereby reducing the amount of circuitry and hardware required by module 10.

When integrating imager 14 and RFID unit 16, module 10 has three principle operational modes: image scanning using imager 14, tag interrogation using RFID unit 16, an interleaved mode that is a combination thereof, and a simultaneous mode. In imaging-only mode, module 10 will capture images and perform the applicable algorithms, such as barcode deciphering, until a barcode is detected or the device is un-triggered. In RFID-only, module 10 will interrogate until a tag is successfully read or module 10 is un-triggered. In interleaved mode, module 10 toggles between imaging and interrogation according to a predetermined timeout schedule. In simultaneous mode, module 10 causes simultaneous imaging and interrogation. In addition, module 10 may be programmed with timeouts to prevent hang-ups. As module 10 can receive, interpret, and execute host commands, these modes may be controlled by a user from host device 38.

Microcontroller 12 may direct RFID interrogation using RFID unit 16 in at least two modes. RFID unit 16 may operate in a free form mode that reads and writes data as a continuous stream, which is limited only by memory capacity. Once RFID unit 16 is triggered, depending on the mode, data is transmitted from the serial port. Second, RFID unit 16 may operate in block mode, where a user may access individual blocks of information via commands sent through interface 18 and interpreted by microcontroller 12.

External control of module 10 is accomplished by a predefined protocol and set of serial host commands that are sent to module 10 from host device 38. The host commands are received by microcontroller 12, which executes the appropriate steps based on the content of the host command. For example, microcontroller 12 may be programmed to recognize host commands that trigger the activation of imager 14 and/or RFID unit 16. Host commands may also be defined to whether the data obtained from imager 14 and/or RFID unit 16 is stored locally in module 10 or passed through interface 18 to host device 38. Host commands may also be provided that enable the various scanning or imaging modes available from imager 14 and RFID unit 16, control the amount of time that imager 14 and RFID unit 16 will attempt scanning before timing out, direct the reading and writing of image and scan data, and select the location where the data is to be written. With regard to imager 14 and RFID unit 16, commands for opening and closing connections to image engine 20 and RFID transceiver 30, as well as commands that return the status of the connection are useful. For example, a host command received from host device 38 may trigger the capture of barcode or RFID data from imager 14 or RFID unit 16. When the scan is complete, a timeout occurs or triggering is turned off via a second host command, and the appropriate feedback is provided to host device 38. The host commands may be preprogrammed into microprocessor 12 and separately provided to host device 38 as a software package for controlling module 10. In addition, software for editing host commands may be supplied to host device 38 to allow a user to edit, add, or delete commands and the corresponding functionality.

Figure 3:
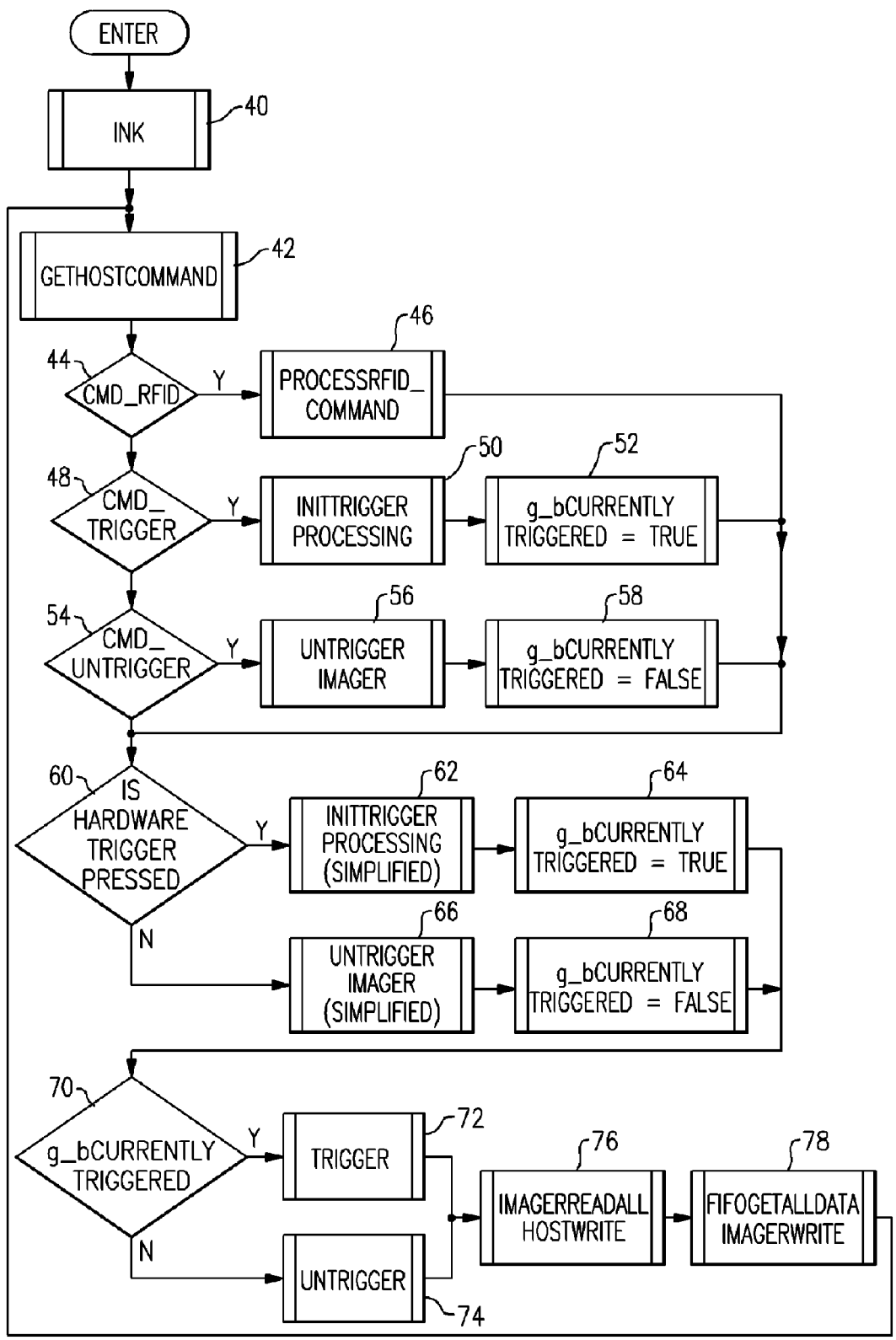
FIG. 3 is a flowchart of main-line processing according to the present invention.

FIG. 3 illustrates an embodiment of main-line host command processing in microprocessor 12 according to the present invention. The specific nomenclature used to define the various routines may be varied by the user or software developer provided that the appropriate functions are performed, and any number of routines and subroutines may be defined and executed in various orders to accomplish image and RFID reading and processing according to the present invention. After initialization 40, microcontroller 12 runs a routine, referred to as GetHostCommand 42, to check whether a host command has been received from host device 38. Upon receipt of a host command, microprocessor 12 checks whether the command is an RFID control command, CMD_RFID 44. If so, the command is processed by routine ProcessRFID_Command 46. If not, a check is performed to see whether the command is a trigger command, CMD_TRIGGER 48. If the command is a trigger command, the appropriate instruction are processed to initiate triggering, InitTriggerProcessing 50 and a variable, referred to as CurrentlyTriggered 52, is assigned the value of TRUE or FALSE depending on whether the selected device has already been triggered. If the command is not a trigger command, a check is performed to see whether the command is an untrigger command, CMD_UNTRIGGER 54. If the command is an untrigger command, the appropriate steps are taken to stop triggering, UnTriggerImager 56, and a variable, CurrentlyTriggered 58, is assigned the value of TRUE or FALSE depending on whether the selected device has already been triggered.

After any of the above processing, microprocessor 12 checks to see whether a hardware trigger has been pressed 60, the triggering processing is performed, InitTriggerProcessing 62, and a variable, referred to as CurrentlyTriggered 64, is assigned the value of TRUE or FALSE depending on whether the selected device has already been triggered. If a hardware trigger has not been pressed 60, the appropriate instruction are processed to stop triggering, UnTriggerImager 66, and a variable, referred to as CurrentlyTriggered 68, is assigned the value of TRUE or FALSE depending on whether the selected device has already been triggered. Finally, microprocessor checks to see whether the CurrentlyTriggered variable is TRUE or FALSE 70, and then calls function Trigger 72 or function UnTrigger 74 as appropriate. Data is then read from imager 14 and written to the host, ImagerReadAllHostWrite 76, and host data that should be routed to imager 14 is written to it, FifoGetAllDataImagerWrite 78.

Figure 4A:
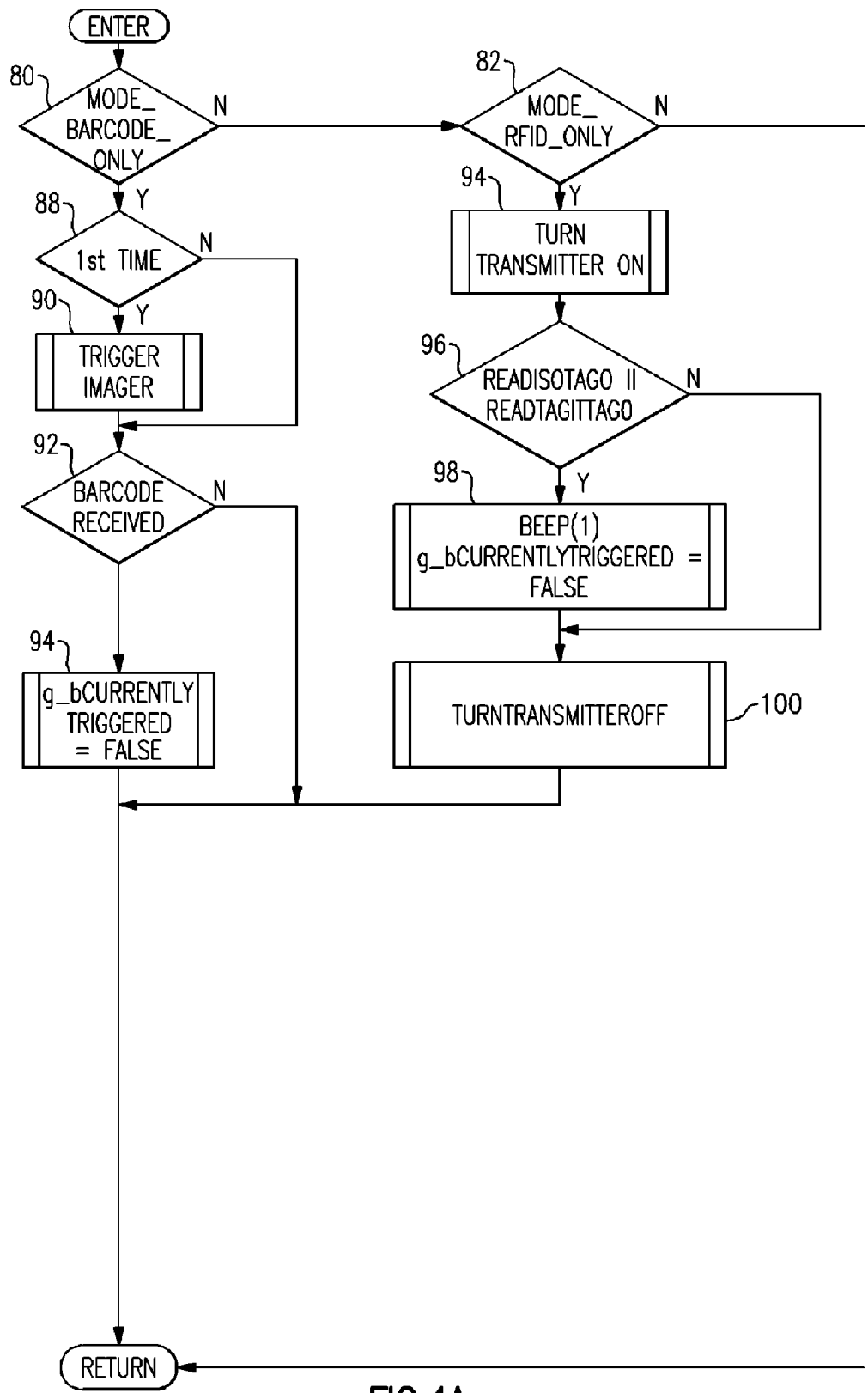
FIG. 4A and FIG. 4B are a flowchart of trigger command processing according to the present invention.
Figure 4B:
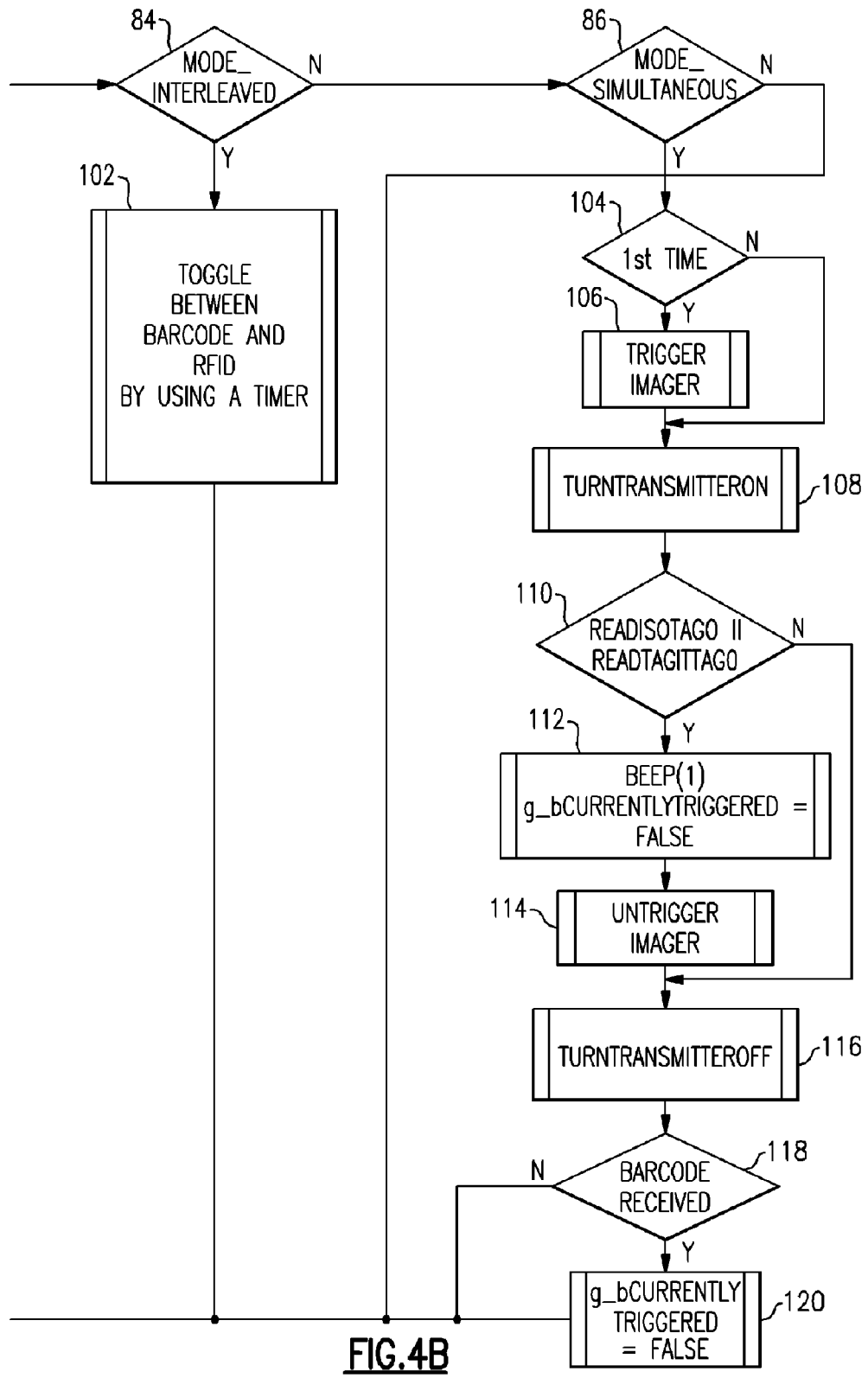

There is seen in FIGS. 4A and 4B, trigger host command processing in microprocessor 12 according to the present invention. Upon receipt of a trigger command, microcontroller 12 first checks to see whether barcode only scanning 80, RFID only scanning 82, interleaved RFID and barcode scanning 84, or simultaneous RFID and image scanning 86 has been previously selected. If bar code only scanning 80 has been selected for the first time 88, and since InitTriggerProcessing 50 has been called, microcontroller 12 triggers imaging 90. If an image is successfully captured and applicable information successfully extracted from the image 92, such as barcode, microcontroller 12 assigns FALSE to the variable CurrentlyTriggered 94. If RFID only scanning 82 has been selected, microcontroller 12 turns the RFID transmitter on 94. If an RFID tag is successfully read 96, an audible tone is sounded and microcontroller 12 sets variable CurrentlyTriggered to FALSE 98. Microcontroller 12 turns transmitter off 100. If interleaved RFID and barcode scanning 84 has been selected, microcontroller 12 toggles operation of imager 14 and RFID unit 16 using a timer 102. If simultaneous RFID and image scanning 86 has been selected, microcontroller 12 checks to see whether the triggering is for the first time 104 and, if so, triggers the imager 106. Transmission from the RFID unit 16 is also turned on 108, and a nearby RFID tag is read 110. If the reading of tag 110 is successful, an audible tone is sounded and variable CurrentlyTriggered is set to FALSE 112. Imager 14 is also untriggered 114 and the transmitter is turned off 116. If the image is successfully processed, e.g., a barcode is received 118, and variable CurrentlyTriggered is set to FALSE 120.

What is claimed is:

1. A combined RFID reader and optical imager for interconnection to a host device, comprising:
    a single printed circuit board;
    a single microcontroller positioned on said printed circuit board and including a command interpreter for processing at least one host command;
    an RFID transceiver positioned on said printed circuit board and attached to said microcontroller;
    an optical imager positioned at least partially on said printed circuit board and attached to said microcontroller;
    a host interface positioned at least partially on said printed circuit board and attached to said microcontroller and configured to receive said at least one host command from said host device; and
    wherein said microprocessor controls operation of said RFID transceiver and said optical imager based upon said at least one host command received through said host interface from said host device.

2. The apparatus of claim 1, wherein said microcontroller is programmed to trigger said RFID transceiver and said optical imager.

3. The apparatus of claim 2, wherein said microcontroller is programmed by the receipt of a first host command to simultaneously trigger said RFID transceiver and said optical imager upon receipt of a second host command.

4. The apparatus of claim 2, wherein said microcontroller is programmed by the receipt of a first host command to alternate triggering of said RFID transceiver and said optical imager based upon receipt of a second host command.

5. The apparatus of claim 2, wherein said microcontroller is programmed to output data collected by said RFID transceiver and said optical imager through said host interface based upon receipt of said at least one host command.

6. The apparatus of claim 2, wherein said microcontroller controls triggering of said RFID transceiver and said optical imager based on receipt of a first host command.

7. The apparatus of claim 6, wherein said microcontroller controls untriggering of said RFID transceiver and said optical imager based on receipt of a second host command.

8. The apparatus of claim 7, wherein said microcontroller controls the location where data obtained by said RFID transceiver and said optical imager is sent based on receipt of a third host command.

9. The apparatus of claim 8, wherein said microcontroller opens a connection to said imager based on receipt of a fourth host command.

10. The apparatus of claim 8, wherein said microcontroller sets a predetermined timeout period for obtaining data from said RFID transceiver and said optical imager said based on receipt of a fifth host command.

11. A method of providing RFID reading and optical imaging for a host device, comprising the steps of:
    attaching to said host device via a host interface a single printed circuit board having a microcontroller, an RFID transceiver attached to said microcontroller, an optical imager attached to said microcontroller, and said host interface attached to said microcontroller positioned thereon, wherein said microcontroller is programmed to interpret commands sent by sent host device through said host interface;
    selectively triggering said RFID reader and said optical imager by sending at least one command from said host device to said microcontroller through said host interface and selectively triggering based upon said at least one command.

12. The method of claim 11, further comprising the step of providing data acquired by said RFID reader and said optical imager to said host device through said single interface.

13. The method of claim 12, wherein said at least one command causes said microprocessor to simultaneously trigger said RFID reader and said optical imager.

14. The method of claim 12, wherein said at least one command causes said microprocessor to alternately trigger said RFID reader and said optical imager.

15. The method of claim 12, further comprising the step of selectively untriggering said RFID reader and said optical imager by sending at least one command from said host device to said microcontroller.

16. A module for collecting information from an object, comprising:
    a printed circuit board;
    a single microprocessor positioned on said printed circuit board;
    a first submodule positioned on said printed circuit board and attached to said microprocessor for obtaining a first type of data from said object;
    a second submodule positioned on said printed circuit board and attached to said microprocessor for obtaining a second type of data from said object;
    a single host interface positioned on said printed circuit board and attached to said microprocessor for interfacing with a host device and receiving host commands sent by said host device; and
    wherein said microprocessor is programmed to selectively operate said first submodule and said second submodule based upon the receipt of a host command from said host device through said host interface.

17. The module of claim 16, wherein said first submodule is an RFID transceiver.

18. The module of claim 17, wherein said second submodule is an optical imager.

19. The module of claim 17, wherein said second submodule comprises a device selected from the group consisting of a laser, a temperature probe, and a scale.

* * * * *